United States Patent [19]

Scoville, Jr.

[11] Patent Number: 4,596,696
[45] Date of Patent: Jun. 24, 1986

[54] DISPOSABLE STERILIZER MECHANICAL AIR REMOVAL TEST PACK

[75] Inventor: John R. Scoville, Jr., Henrietta, N.Y.

[73] Assignee: Sybron Corporation, Rochester, N.Y.

[21] Appl. No.: 551,857

[22] Filed: Nov. 15, 1983

[51] Int. Cl.[4] .................. A61B 19/02; B65D 81/00; C12Q 1/22; G01N 21/78
[52] U.S. Cl. ..................... 422/61; 116/207; 206/204; 206/438; 206/439; 206/459; 374/104; 374/162; 422/56; 422/58; 435/31; 435/311
[58] Field of Search ............... 436/1, 164, 166, 169; 422/56, 58, 61; 206/438–440, 484.1, 204, 459; 374/162, 104; 435/31, 311; 116/207

[56] References Cited

U.S. PATENT DOCUMENTS

| | | | |
|---|---|---|---|
| 3,951,333 | 4/1986 | Forbes, Jr. et al. | 206/438 |
| 4,145,186 | 3/1979 | Andersen | 422/57 |
| 4,194,622 | 3/1980 | Lewis | 436/1 |
| 4,367,816 | 1/1983 | Wilkes | 206/484.1 |
| 4,486,387 | 12/1984 | Augurt | 422/58 |

FOREIGN PATENT DOCUMENTS

| | | | |
|---|---|---|---|
| 0069037 | 1/1983 | European Pat. Off. | 435/31 |
| 7412980 | 4/1976 | Netherlands | 206/439 |

Primary Examiner—Barry S. Richman
Assistant Examiner—C. M. Delahunty
Attorney, Agent, or Firm—Robert A. Gerlach; Owen D. Marjama

[57] ABSTRACT

A disposable sterilizer mechanical air removal test pack comprising an outer container in the form of a box having a definite shape and being formed of a relatively air and steam permeable material coated with a form-stabilizing layer of a relatively air and steam impermeable material, and a body of relatively air and steam permeable material enclosed in the box. An indicator means is arranged in the body of material for indicating when contact with steam has taken place. The box includes a plurality of closure flaps which provide interruptions which control and direct the flow of steam into and air out of the interior of the body of material with the flow of steam and air occurring predominantly in a lateral direction through the body of material.

10 Claims, 9 Drawing Figures

DISPOSABLE STERILIZER MECHANICAL AIR REMOVAL TEST PACK

BACKGROUND OF THE INVENTION

This invention relates to high vacuum sterilizer testing using a test pack. Such testing and a standard test pack therefor are prescribed by the Association for the Advancement of Medical Instrumentation (AAMI) in AAMI ST. 1-1980 entitled Good Hospital Practice: Steam Sterilization and Sterility Assurance. The AAMI test pack is essentially a body of material made up of articles which are the same as, or quite like, articles which are commonly sterilized in high vacuum sterilizers. In particular, o the body of material may be a stack of folded similar towels, perhaps tied in a bundle, variously called a towel pack, or a Bowie-Dick type test pack, which has a heat-sensitive indicator in some inner portion thereof. Typically, this indicator will be a sheet of material sandwiched in the towels and having the same area as one of the towels as folded. The sheet of material will be covered by a chemical which undergoes a lasting visual change at every point thereof attaining a given temperature.

In operation, the test pack is placed in the sterilizer and subjected to a high vacuum in order to remove air from the towels which, of course, are porous and so tend to be saturated with any ambient fluid medium. Freed from air, the pack is next subjected to steam which is supposed both to penetrate the interstitial space of the towel material making up the test pack and to transfer sterilizing heat to the fibers of that material.

As in known, particles or bubbles or pockets of air contacting portions of material of the test pack insulate the affected material from the steam. If one supposes that there has been effective removal of air due to the mechanical effect of the high vacuum, then one might also suppose that the heat-sensitive material covering of the indicator would reflect this by exhibiting everywhere visually-detectible change due to steam contacting it everywhere. However, if there had been air contacting any part of the coating during steam application to the test pack, then one would suppose that less or no change would be detectible visually at such part.

Inasmuch as articles, materials, etc., which the sterilizer normally receives for sterilization, normally only differ from a test pack in their response to the vacuum and steam treatment cycle by not showing signs of exposure to heat, one supposes therefore that if a test pack subjected to a treatment cycle indicates that all air has been effectively been removed from it and that the steam has contacted every possible particle thereof, then the sterilizer will be effective both to remove air effectively and sterilize properly the aforesaid articles, materials, etc.

The above-said towel-pack testing is described in detail by AAMI ST. 1-80, pages 8, 9 and 10, and, as well, by J. H. Bowie et al in their article "The Bowie and Dick Autoclave Tape Test", The Lancet, Mar. 16, 1963, pages 586 and 587. Here, the towel pack is described as being reusable, subject to being reconditioned after each use. Inasmuch as it is customary to perform the test once daily, or oftener, workers in the art have also devised inexpensive test packs which nevertheless for test purposes are effectively equivalents of the standard towel packs, and are disposable after a single use, and are, stockable and need little or no preparation for use. In one case, the Bowie et al "29 huckaback towels" were replaced by a number of 9"×12" sheets of absorbent paper stacked about ¾" inch high. In the middle of this stack was an indicator consisting of one 9"×12" inch sheet of paper, one side of which was coated with heat sensitive material in a distinctive pattern covering the entire surface of that side. The pack was completed by a crepe paper wrapping secured by a fastener in the form of a piece of sticky tape having a heat sensitive coating on the side opposite its sticky side.

When this prior art test pack is subjected to the test cycle, the heat sensitive material on the fastener shows whether or not the pack had been exposed to heat. If exposure to heat is indicated, then the crepe paper wrapping will be opened to permit getting at the indicator sheet in the middle of the paper stack and inspecting it to see if the steam had contacted the entire surface of the indicator sheet. Complete exposure, and therefore effective air removal would be indicated if the entire pattern of heat sensitive material had changed its appearance substantially uniformly, e.g., from a light colored pattern barely distinguishable from that of the side of the paper on which the pattern was laid, to a pattern entirely of a black or very dark color contrasting strongly with the paper color. Where, if anywhere, air was present next to the indicator sheet's coated surface, no or little color change would have occurred and this would be immediately noticeable as a light-colored interruptions of the otherwise darkened pattern.

With this test pack, the absorbent paper would be chosen in characteristics (nature, porosity, basis weight, etc.) and quantity, such that the paper stack is equivalent to the towels in respect of air and steam permeability. The crepe paper wrapping, and the paper of the indicator sheet in the stock, themselves make no appreciable contribution to performance of the pack. The central location in the stack of the indicator sheet makes its character irrelevant, whereas the crepe paper, for example, surgical crepe, so-called, is relatively transparent to steam.

SUMMARY OF THE PRESENT INVENTION

I have devised a test pack which functions in a manner similar to the prior art test packs described above, and which is structurally similar to the prior art test pack with respect to utilizing a stack of paper. However, the prior art's towel pack and crepe-wrapped test pack are contained in materials (wrappings) which have little effect on the rate at which steam has ingress to, and air finds egress from, the interior of the test pack. According to my invention, however, it is the container which is the major determinant of that rate.

In particular, such a container according to my invention may be a box of paste board, or equivalent sheet material, having a stack of steam and air permeable absorbent paper therein, said box being about the shape and volume of a stack of absorbent paper contained therein. The paste board used is relatively transparent to steam and it has a number of holes which are punched through it. However, the rate of steam ingress and air egress is determined by crevices, interrupting the continuity of the walls of the box, which result from folding a piece of the paste board into box form, and a film relatively impermeable to steam and laminated to one side of the paste board. This film may be, e.g., a polyester film. In other words, the rate of the steam and air ingress and egress is determined by the film and the crevices.

According to my invention, my test pack also differs from the prior art by being contained in a container which not only has a definite shape, but is made of a material which, once formed into that shape, makes that shape stable both when the container is exposed to ordinary ambient conditions (e.g. atmospheric pressure, room temperature) and after it has been subjected to high vacuum/vacuum purge and steaming in a sterilizer.

In particular, the material which has shape stability is the same polyester film/paste board laminate, which controls air and steam egress from and ingress to the paper stack, as explained supra.

My invention may also provide for incorporating various useful features into the box. Thus, it may provide for a tear strip, which makes access to the paper stack neat and less destructive than in the case of a crepe wrapper. Again, the tear strip may provide for record keeping. The exterior surface of the box allows the printing of directions, exemplary test patterns thereon, and as well provides for supporting a suitable means for indicating whether the test pack had been exposed to heat.

Due to its form stability, and its compact and definite shape my novel test pack can be conveniently handled and stored both prior to test use and thereafter. The crepe paper wrapped test pack once used and opened, becomes a disorganized and unhandy mass of wet paper, which one will wish to discard quickly after noting down separately the results of the test. With my novel test pack, the tear strip provides the record receiving medium, while the test pack itself after use is still in a condition in which it can be as conveniently and easily handled or stored as before exposure to the sterilizer treatment cycle.

BRIEF DESCRIPTION OF THE DRAWINGS

N.B. Each of FIGS. 6 through 9 is to scale, but only FIGS. 6 and 7 are to the same scale.

DETAILED DESCRIPTION OF THE PREFERRED EMBODIMENTS OF MY INVENTION

Referring to FIGS. 1, 6, 7 and 8, a test pack of the preferred form is designated generally by the reference character P. Test pack P consists essentially of the box 1 and a stack S of sheets of nearly the dimensions of box 1 (itself about 9" × 12" × ¾", for example.) Stack S has a thermal indicator sheet T therein.

Box 1 is of conventional shape but, according to my invention, has a tear strip 2 arranged to allow easy and minimally destructive access to the box. Thus, as will be seen from FIGS. 1 and 6, the one end panel 3 of the box is formed by a flap 4. Flap 4 is a continuous extension of the bottom panel 5 and is folded over so that it can be tucked under the free edge 6 of top panel 7 of box 1.

Figure 1:
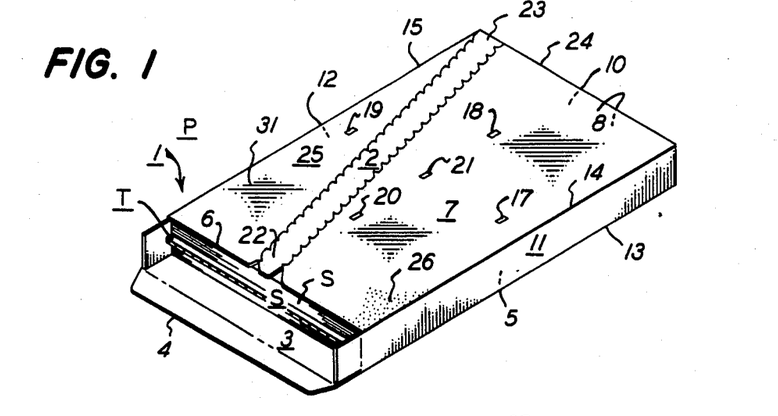
FIG. 1 is a perspective view of one form of my invention.

The other end panel 8 of the box is likewise provided by a flap 9 (not indicated in FIG. 1). Flap 9 is a continuous extension of the top panel 7 and is folded over so that it can be tucked under the free edge 10 of panel 5.

The remaining panels, 11 and 12, along with panels 5 and 7 are basically formed from a single sheet of material having four parallel straight folds 13, 14, 15 and 16 and a slight overlap of opposite ends (not shown in FIG. 1) of the material, which are glued or otherwise fastened together.

In order to preserve definiteness of resulting shape defined by the six rectangular panels 3, 5, 7, 8, 11 and 12, I use a form-stable material, preferably clay coated, solid bleach sulfate paperboard stock, preferred caliper 0.020 in., a tolerable range being 0.018 in. to 0.022 in., or equivalent material, to which is laminated a 1.25 mil polyethylene terephthalate polyester film, or equivalent. The film will be on the inside of the box. The paperboard, of course, assures that the box 1 will keep its shape in storage at normal conditions of room temperature, humidity and pressure, while the polyester provides a semi-permeable barrier which serves to control the rate at which air and steam are allowed to enter or exit the pack.

Without the polyester film lamination, the paste board stock is relatively transparent to the steam. The polyester film also extends its form stability to steam sterilizing cycle conditions. Some convenient number and distribution of holes or slots, as indicated at 17, 18, 19, 20 and 21, may be provided to allow air egress and steam ingress to the interior of box 1.

The one end 22 of tear strip 2 begins at edge 6 at a place intermediate its ends. The other end 23 of tear strip 2 is the corner of panel 7 at the intersection of fold 15 with the fold 24, fold 24, of course, resulting from the provision of panel 8.

The resulting orientation of tear strip 2 provides the aforementioned easy and minimally destructive access to the contents of box 1. Thus, to inspect the contents of box 1 after it has gone through a sterilizing cycle, one need merely tear out the strip 2. This everywhere frees a flap 25, consisting of about one third or so of panel 7, except at the folds 15 and 16, which being straight, provide hinges about one or both of which the flap 25 can be deflected, depending on the presence or absence of locking tabs, indicated at 27, 28, 29 and 30; whether or not glue is used to secure the panels 3 and 8 in place; and so on. If glue is used, edge 6 will not be literally free, but may be considered free in a practical sense because one will be able to relatively easily peel flap 25 from flap 4.

Figure 6:
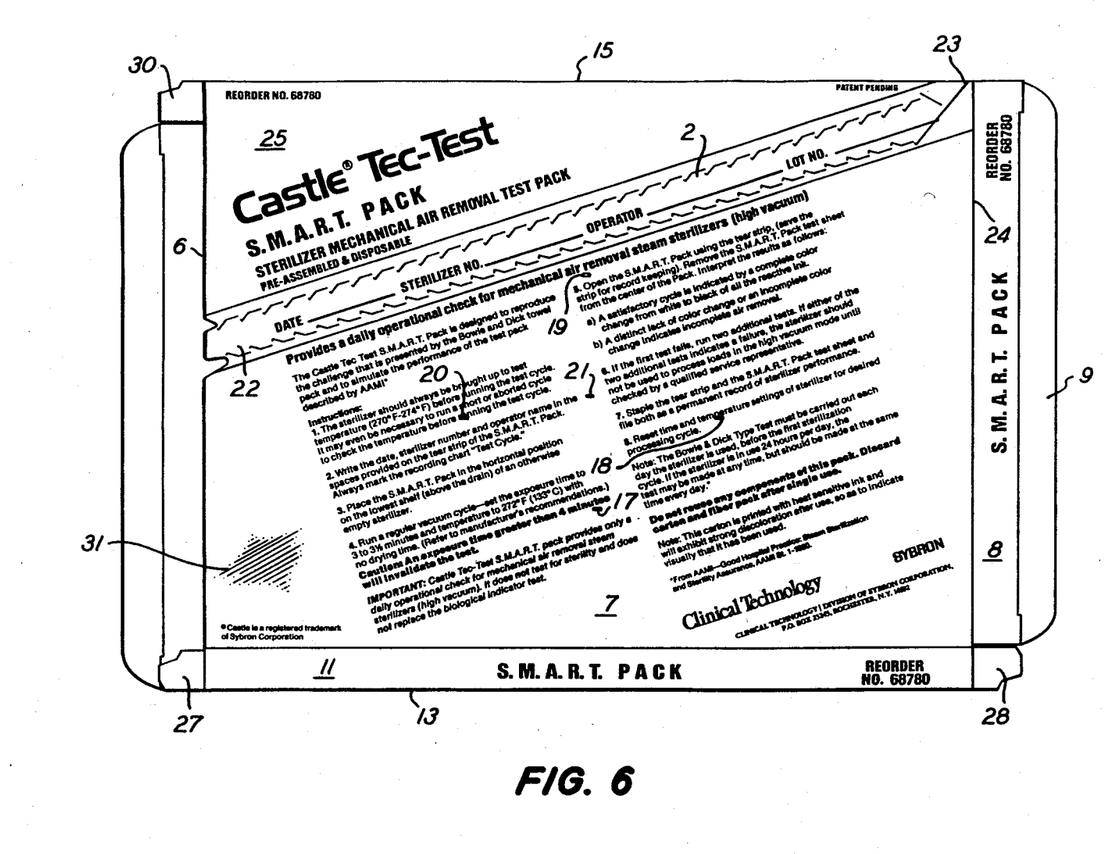
FIGS. 6 and 7 are top and bottom plan view of the commercial version of the form of my invention shown in FIG. 1.
Figure 7:
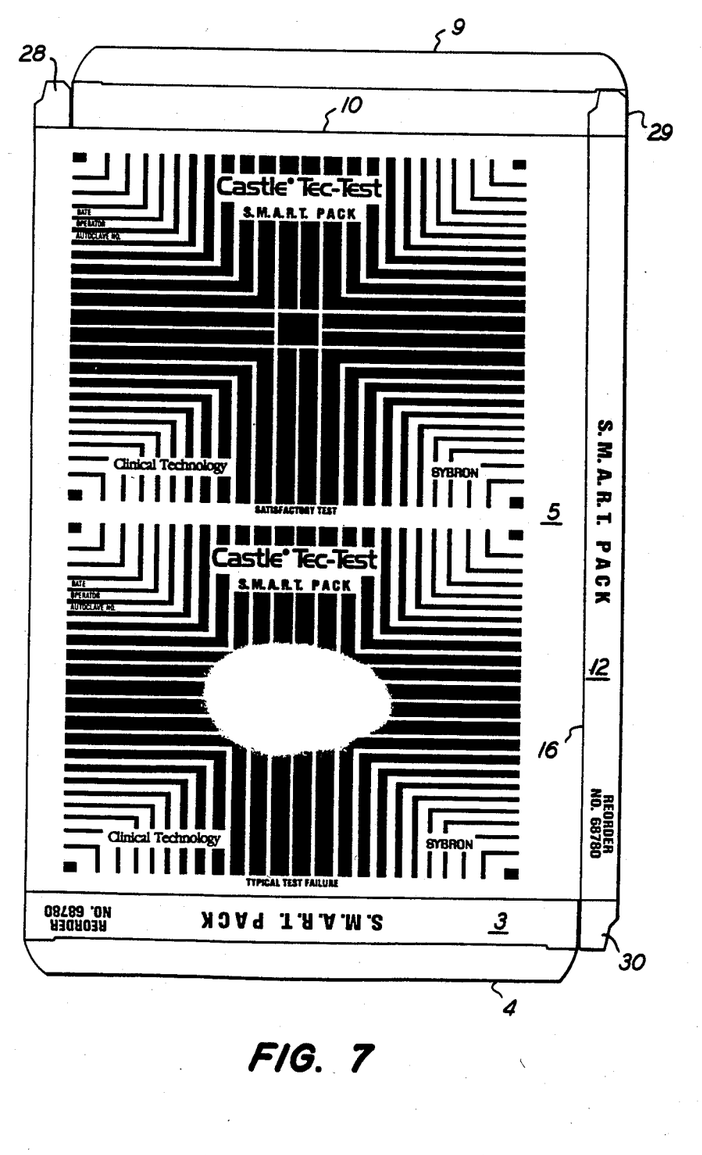

As will be seen from FIGS. 6 and 7, panels 5 and 7 bear indicia expressive of various kinds of intelligence. Thus, panel 5 bears sample test patterns, one, labeled SATISFACTORY TEST exemplifies the effect of uniform steam treatment, and the other, labeled TYPICAL TEST FAILURE, shows how an indicator would look if air, at the center of the test pack, kept the thermally sensitive material of the indicator (not shown) from being contacted by steam at the center of the test pack. In use, of course, one removes tear strip 2, pulls flap 25 away from the top of the pack, lifts the pack at least partly out, and removes the indicator therefrom, a sheet of paper twice the size of the sample test patterns, but resembling one or the other a great deal, depending on the effectiveness of air removal.

Panel 7 bears thereon sundry self-explanatory information, the major portion being a succinct account of air removal testing instructions according with AAMI ST. 1-1980, told from the point of view, so to speak, of a test pack according to my invention. According to the invention, test strip 2 provides for receiving intelligence relating to the specific testing situation, and so constitutes a record as well as a means of easy and relatively non-destructive access to the indicator. One other feature of the invention, represented by stippling 31, in FIG. 1 and FIG. 6, is a contrasting background (e.g., blue under the black printing of the intelligences on panel 7), which will undergo a more or less permanent and visually-discernable change in appearance, but without affecting the readability of the intelligence.

Figure 2:
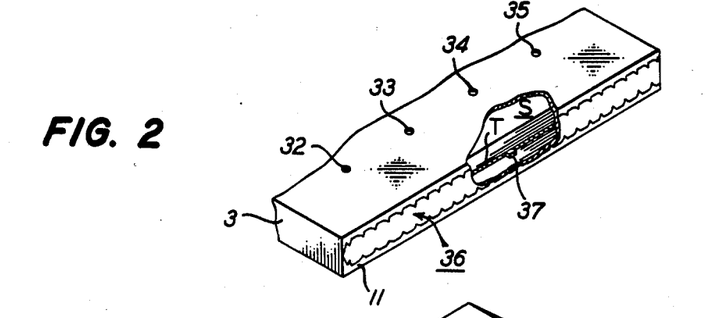
FIG. 2 is a fragmentary perspective view of a modified version of the FIG. 1 form of my invention.

FIG. 2 shows a modification of FIG. 1 in respect of having round holes 32, 33, 34 and 35, instead of rectangular holes 17 through 21, and in having a tear strip 36 in panel 11 and extending along the whole length thereof. FIG. 2 also shows a detail not evident from FIG. 1 and that is the tab 37. Tab 37 is an integral part of indicator sheet T. While FIG. 1 shows the sheet T as protruding slightly from stack S, in practice sheet T is the same in dimension as the stack and aligned with the other sheets therein, so it is convenient to provide the tab 37 in order to facilitate access to sheet T which, in terms of FIG. 1 would be at the side of stack S adjacent panel 12.

Figure 3:
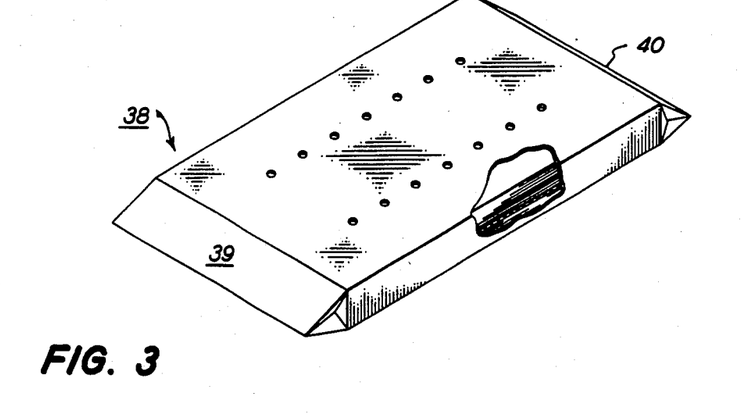
FIG. 3 is a perspective view of a second form of my invention.

In the form of the invention shown in FIG. 3, I contemplate housing the stack S in a plastic shell or bag 38. Like in FIGS. 1 and 2 suitable holes and a tear strip (not shown in FIG. 3) may be provided. The bag 36, while made from a plastic such as polyester, polypropylene, nylon, laminates, etc. (and which can be transparent if desired,) would not be as definite in form as the pasteboard box 1 of FIGS. 2 et al. However, by closing the ends 39 and 40 of the bag 38 by heat sealing or adhesive, as is conventionally done in the plastic film, packaging art, allows preservation of substantial form stability due to access being provided by a tear strip preferably arranged and dimensioned like strip 36, FIG. 2, in a bag side corresponding to the panel 11 of FIG. 2, thereby to minimize the disruptive effect of opening the bag.

Figure 4:
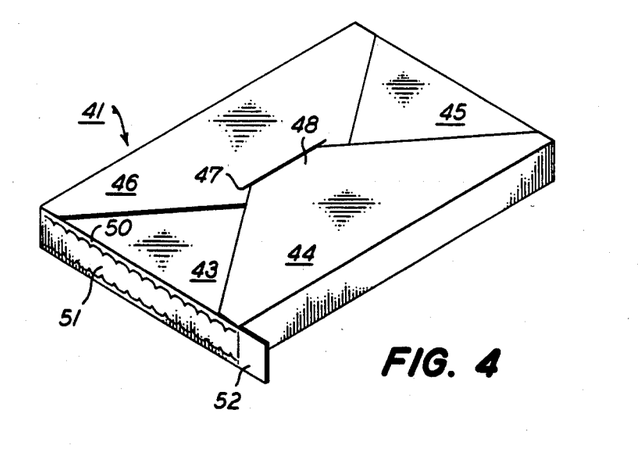
FIGS. 4 and 5 are perspective views of a third form of my invention.
Figure 5:
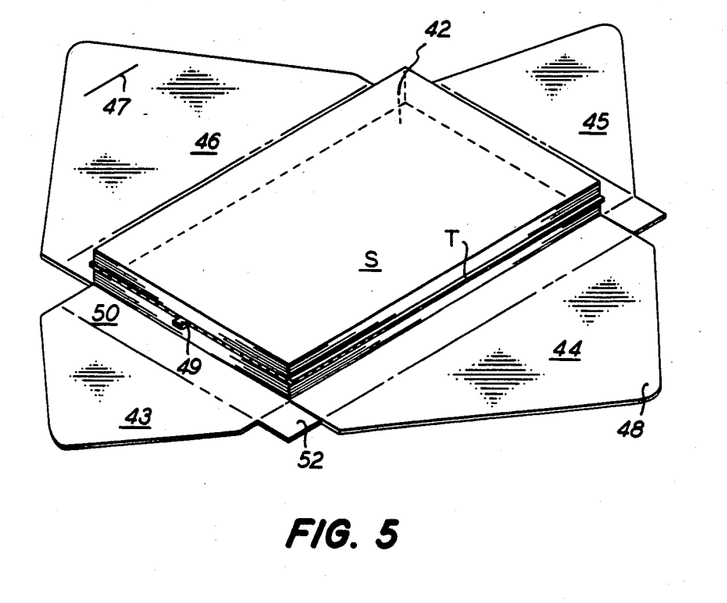

In the form of the invention shown in FIGS. 4 and 5 the stack S is contained in a box 41, formed of a rectangular bottom panel 42 (shown only in FIG. 5 and somewhat figuratively but having substantially the form and dimensions of the stack sheets) and having more or less triangular flaps 43, 44, 45 and 46, which extend from the sides of panel 42. When folded over, the flaps form five panels corresponding in form and dimension to panels 3, 7, 8, 11 and 12 of FIG. 1. Flap 46 has slot 47 therein, through which the top 48 of flap 44 slips for securing all the flaps together in roughly planar form.

As shown in FIG. 5 thermal indicator sheet T appears to be a little larger all around than the other sheets in stack S, and thereby would be very readily located and manipulated merely by opening the flaps to the state of FIG. 5. However, I prefer to provide Sheet T with a tab 49, and a tear strip 51 (not shown in FIG. 5) in the panel 51 (which is part of flap 43) actuated by a pull 52 forming one end of the strip. The tear strip will obviate opening the flaps 43, 44, 45 and 46, although that is a not unlikely mode of access to the indicator sheet T. In contrast to unwrapping the prior art crepe-wrapped test pack, which leaves one with a somewhat dank, limp, and amorphous mass, not readily handled unless to throw it away, opening the flaps 43, 44, 45 and 46 does not affect the shape stability of the box 41, although it changes its shape.

Figure 8:
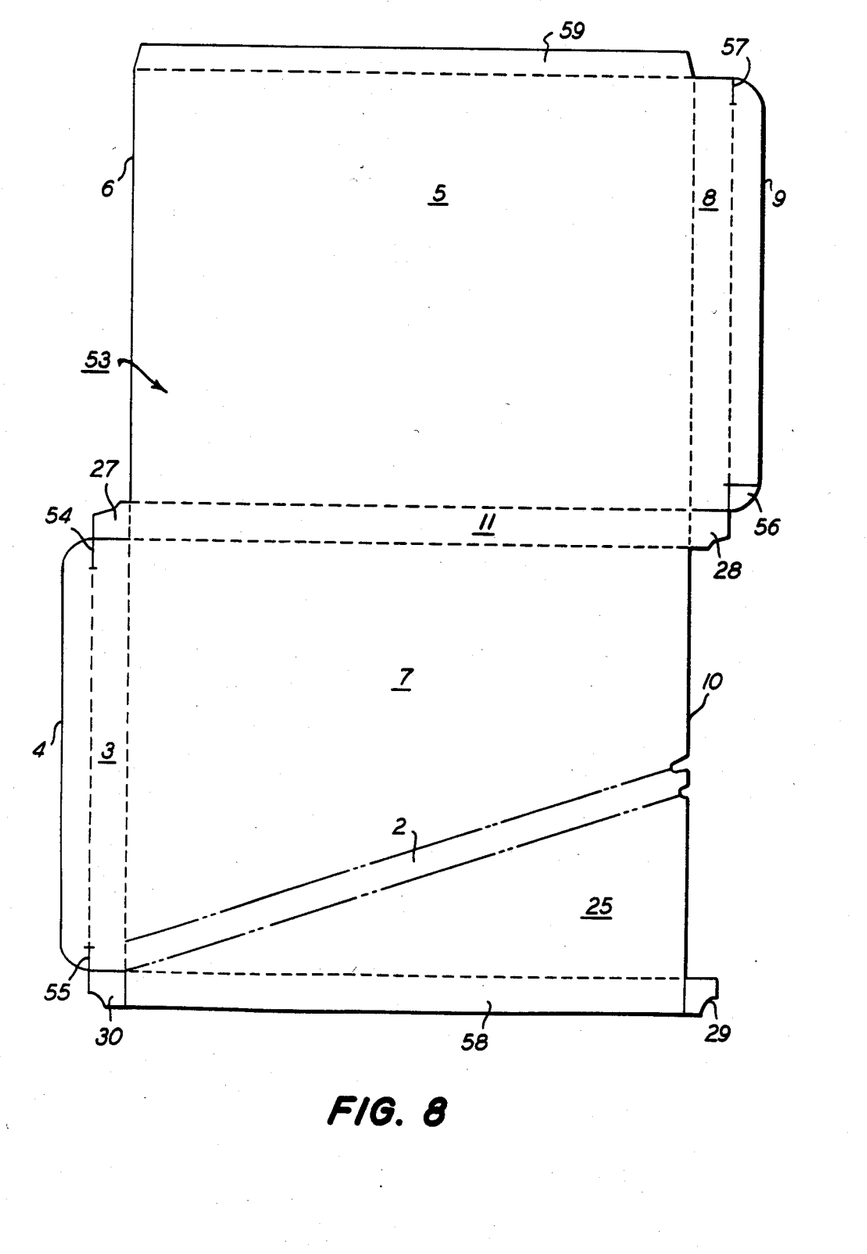
FIG. 8 is a plan view of a blank used in constructing the form of my invention shown in FIGS. 6 and 7.

FIG. 8 shows a flat blank 53 for forming the box 1 of FIGS. 1, 6 and 7 (and a box of FIG. 2, except for tear strip location). FIG. 8 is largely self-explanatory, but it should be noted that the locations of folds are shown in dashed lines indicating their direction, and that cuts in the box flaps are indicated at 54, 55, 56 and 57. These cuts cooperate with the flaps 4 and 9, and with locking tabs 27, 28, 29 and 30, such as to positively secure the tabs when the tabs are inserted in the box ends. Also, the tear strip 2 is shown mainly as to location, and in any event is not formed into the material of the blank until the printing, etc., of the panels has been completed.

In folding blank 53 into box form, its flaps 58 and 59 are overlapped and glued together, whereby to form panel 12.

Figure 9:
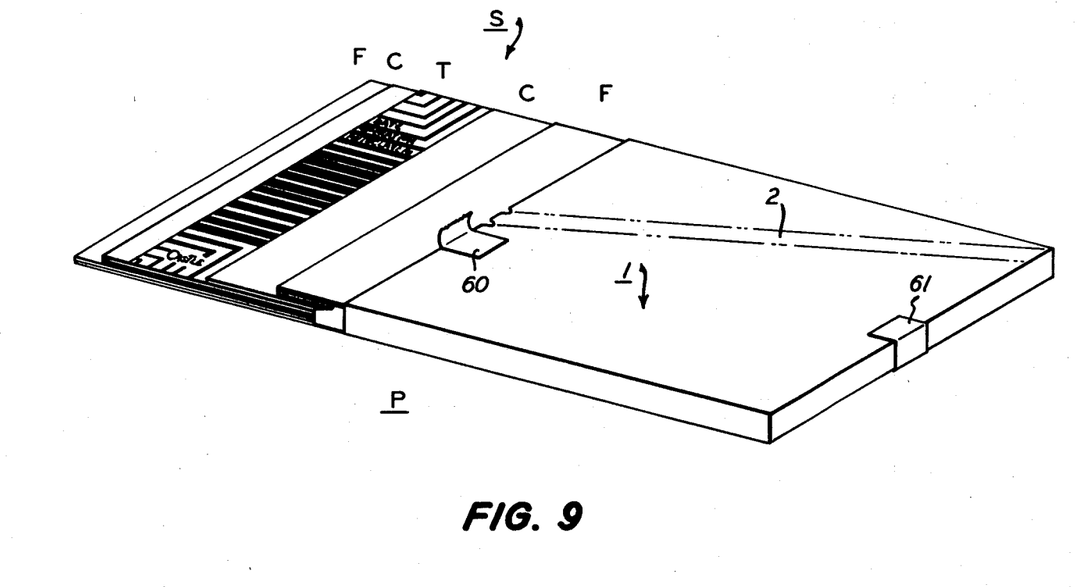
FIG. 9 is a perspective view of the form of my invention shown in FIGS. 6 and 7, in partially-disassembled form.

In FIG. 9, reference numerals 60 and 61 identify heat and moisture stable strips of sticky tape, preferably transparent Mylar or the like, which maybe used as shown in FIG. 9 to assure that the flaps stay tucked into the ends of box 1.

More importantly, FIG. 9 shows the specific make up of stack S. Thus, in accordance with my invention, one single thermal indicator sheet T is between two 4-sheet layers C of control sheets, which in turn, are sandwiched between two 10-sheet layers F of filler sheets. While heretofore it was known to use no filler sheets, or to provide the control sheets on the outsides of the stack and the filler sheets in the middle, these prior configurations do not seem to emulate a Bowie-Dick Test Pack as well as does the stack configuration according to my invention.

The various kinds of paper used in these sheets have the following characteristics.

| STACK PAPER SPECIFICATIONS | | | |
| --- | --- | --- | --- |
| | Control | Filler | Indicator |
| Basis Weight (lb/3000 ft$^2$) | 210 + 10 | 65 + 3 | 83 + 3 |
| Caliper (inch) | 0.020 + 0.002 | 0.020 + 0.002 | 0.0043 + 0.0005 |
| Gurley (5 oz/100 cc/sec.) | 35 + 10 | — | 13 + 6 |
| Frazier (ft$^3$ per min.) | — | 80 + 20 | — |

N.B. All plus signs supra should be plus-or-minus signs.

The paper should not be bone dry when the pack is put into the sterilizer, as that can compromise the test results.

The heat sensitive material is a proprietary ink formulation of the Propper Manufacturing Company, Long Island City, Long Island, N.Y. 11101. Yellowish in color at room temperature and before exposure to higher temperatures, it should completely react to sterilization temperature by permanently turning solid black if placed in a steam autoclave and subjected to the following cycle:

1. Pre-vacuum, to 20" Hg
2. Steam bleed, to 10" Hg
3. Pre-vacuum, to 20" Hg
4. Steam bleed, to 10" Hg
5. Pre-vacuum, to 20" Hg
6. Steam, to 272° F.+2° F. for 3½ minutes (stopwatch)
7. Evacuate, to 20" Hg This particular ink, if subjected to an abbreviated cycle, like the above cycle, but having but a single pre-vacuum step prior to steps 6 and 7, and no steam bleed at all, will permanently turn to a brownish color not deeper than a dark tan. This is because the ink quantity and formulation require a certain amount of heat from the steam in order to develop the full color change. The rate at which steam gains access to the ink is controlled by the box and, to a lesser extent, the control sheets C. As the present box has been designed for use in a sterilizer having the full cycle described above, therefore, using it in the abbreviated cycle, doe not allow enough heat for full color change.

In other words, this particular ink formulation allows detection of incomplete cycles as well as the imperfect removal of air. However, I do not regard cycle completeness capability as essential, as the main concern here is determined whether or not air is being effectively removed. Furthermore, analysis of the cycle is preferably carried out by recording the temperature in the sterilizer throughout the cycle. Nevertheless, regardless of the degree of color change, it is only the uniformily thereof over the sheet T which is affected by the imperfect removal of air, although, obviously, if the entire surface of the sheet were covered with air, and this air did not get removed, there would be uniformly little or no color change.

As previously noted, the nature of the paper of indicator sheet T is not relevant, insofar as is concerned ingress/egress of steam/air to the stack interior. However, in this regard, the box 1 and the stack S as a whole together have to closely simulate the classical Bowie-Dick Test Pack. It is important to note that neither the Bowie-Dick Test Pack nor my novel test pack can be taken as an indication of effective sterilization. All that it is tested for is air removal, and nothing more.

In my invention, the box 2 is the major determinant of ingress/egress, and control sheets act as the main minor determinant. The filler sheets are provided merely for their bulk, and have much less effect than the control sheets on steam/air ingress/egress.

As for the box 1 itself, ingress/egress of steam/air is mostly through the crevices created by inserting the flaps in the ends of the box (unless these flaps are glued in place, in which case equivalent provision, like relatively good sized holes or slots, must be provided in box 1). To a much lesser extent do holes 17, 18, 19, 20 and 21 affect ingress/egress. Thus in the box shown in FIGS. 6 and 7, there are five identical holes like 17 through 21 in each of panels 5 and 7, but doubling their number would not appreciably change performance. Likewise, the tear strip 2, being a cut-out, will allow a certain amount of egress/ingress, but it is not substantial, especially as the cut-out is at least partly sealed by the plastic film on the inside of the box. The flow or ingress/egress of steam/air through the box occurs predominantly in a lateral or horizontal direction through and between the permeable stack interior. The film is not impervious, but its contribution to steam ingress, is much less than the paste board would allow if not coated.

The sheet T, FIG. 9 shows the legends DATE, OPERATOR, AUTOCLAVE No.; which are variants of the legendry shown on strip 2 in FIG. 6. When a test pack is used, some record is customarily kept, which could take the form of tear strip 2 with the blanks filled in, by itself, or stapled to the indicator sheet T itself. Again, the content of the blanks of the tear strip could be transferred to the indicator sheet T itself, and the tear strip discarded. One might even preserve the whole used test pack as a record since the material of box 1 is water-resistant and will not, therefore, be objectionably moist, and due to its form stability, will still be in compact, readily-handled, and storable condition.

The indicia on the several panels of box 1 are printed preferably in a conventional black printers ink on a field of ink of a contrasting color, which when coated with transparent varnish, will respond to sterilizer heat, by visibly changing in appearance. One such ink, which fades in response to sterilizer heat, and which I use as indicated at 26 in FIG. 1, is PMS 292 blue, as provided by Westvaco, Folding Carton Divison, 2000 Ogletown Road, P.O. Box 8095, Newark, Del. 19711. The varnish itself has no influence on the permeability of the box to steam.

Obviously, the make-up of test pack according to my invention may vary in respect to paper characteristics, numbers of sheets, heat sensitive materials for the indicator sheet T, etc. Save to the extent one detail or another may restrict a claim or several claims infra, my invention is not to be regarded as restricted to such detail. My novel test pack will be generally useful on any sterilizer subject to operational standards in accordance with Bowie-Dick principles, although it may be subject to modification of its structural parameters in various respects on account of sterilizer cycle differences, such as exemplified by the two test cycles described above in terms of their effects on the indicator sheet T. However, I would consider such modifications within the scope of the claims set forth herein below.

Having described my invention in conformity with 35 USC, Section 112, I claim:

1. A disposable sterilizer mechanical air removal test pack, said pack comprising an outer container in the form of a box having a definite stable shape and being formed of a relatively steam and air permeable material coated with a form-stabilizing layer of a relatively steam and air impermeable material, and a body of steam and air permeable material having indicator means arranged to be contacted by steam permeating said material during a steam high vacuum/vacuum purge sterilizing cycle of a sterilizer for indicating whether such contact with steam has taken place and to what extent, if any, air was present in said material and interfered with such contact with steam; said body being enclosed in said box and said box being constructed to include a plurality of closure flaps which provide interruptions which control and direct the flow of steam access to and air egress from the interior of said body, with said steam and air flow occurring predominantly in a lateral or horizontal direction through and between said body of relatively steam and air permeable material, wherein said form-stabilizing layer causes the shape of the box to remain stable during and following exposure of said box to said steam sterilizing cycle.

2. The disposable sterilizer mechanical air removal test pack of claim 1, wherein said box is made of a paperboard sheet material and said form-stabilizing layer comprises a plastic film fixed to said paperboard and being of a thickness effective to stabilize the shape of said box.

3. The disposable sterilizer mechanical air removal test pack of claim 1, wherein said box is made of a relatively steam and air permeable sheet material and said form-stabilizing layer and wherein said form-stabilizing layer comprises a plastic film fixed to one side of said relatively steam and air permeable sheet material.

4. The disposable sterilizer mechanical air removal test pack of claim 1 wherein said form-stabilizing layer comprises a polyester film fixed to one side of said relatively steam and air permeable material.

5. The disposable sterilizer mechanical air removal test pack of claim 1, wherein control and direction for steam access to and air egress from the interior of said body of relatively steam and air permeable material is aided by further including a plurality of holes in said box.

6. The disposable sterilizer mechanical air removal test pack of claim 1, wherein said box includes a tear strip portion providing ready access to said body of relatively steam and air permeable material.

7. The disposable sterilizer mechanical air removal test pack of claim 1, wherein the outer surface of said box includes a field of visually readable, intelligence-bearing, heat sensitive material thereon, said heat sensitive material being responsive to temperature for causing a visual lasting change in appearance of said field without obscuring said intelligence, such change signifying exposure of the test pack to the heat of said sterilizing cycle.

8. A disposable sterilizer mechanical air removal test pack, said pack comprising an outer container in the form of a box having a definite stable shape and being formed of a relatively steam and air permeable material coated with a form-stabilizing layer of a relatively air impermeable material, said box having a plurality of edge or side surfaces and a planar top and bottom surface, and a body of relatively steam and permeable material having indicator means arranged therein to be contacted by steam permeating said body of relatively steam and air permeable material during a steam high vacuum/vacuum purge sterilizing cycle of a sterilizer for indicating whether such contact with steam has taken place and to what extend, if any, air was present in said body of relatively steam and air permeable material and interfered with such contact with steam; said body being enclosed in said box and said box being constructed to include a plurality of closure flaps positioned at the edges of said box and which closure flaps provide interruptions which control and direct the flow of steam access to and air egress from the interior of said body, wherein said form-stabilizing layer causes the shape of the box to remain stable during and following exposure of said box to said steam sterilizing cycle.

9. The disposable sterilizer mechanical air removal test pack of claim 8, wherein said box is made of a relatively steam and air permeable sheet material and said form-stabilizing layer and wherein said form-stabilizing layer comprises a plastic film fixed to one side of said sheet material.

10. The disposable sterilizer mechanical air removal test pack of claim 9 wherein said form-stabilizing layer comprises a polyester film.

* * * * *